(12) United States Patent
Shieh

(10) Patent No.: US 6,264,620 B1
(45) Date of Patent: Jul. 24, 2001

(54) BLOOD SYRINGE

(76) Inventor: Iou-Der Shieh, No. 22, Tou-Lun Lane, Tou-Lun Li, Lu-Kang Chen, Changhwa Hsien (TW)

( * ) Notice: Subject to any disclaimer, the term of this patent is extended or adjusted under 35 U.S.C. 154(b) by 0 days.

(21) Appl. No.: 09/511,064

(22) Filed: Feb. 23, 2000

(51) Int. Cl.$^7$ ........................................... A61B 5/00
(52) U.S. Cl. ............................ 600/576; 604/110
(58) Field of Search ........................... 600/573, 576, 600/578, 579; 604/110

(56) References Cited

U.S. PATENT DOCUMENTS

| | | | |
|---|---|---|---|
| 3,951,146 | * | 4/1976 | Chiquiar-Arias ..................... 604/110 |
| 5,370,620 | * | 12/1994 | Shonfeld ............................. 604/110 |
| 5,540,660 | * | 7/1996 | Jenson ................................ 604/110 |

* cited by examiner

Primary Examiner—John P. Lacyk
Assistant Examiner—Pamela L. Wingood
(74) Attorney, Agent, or Firm—Rosenberg, Klein & Lee

(57) ABSTRACT

A blood syringe includes a hollow barrel an external thread formed on one end and a circular internal flange formed on the inside of the other end. A piston with a hollow stub extending from one end is slidably mounted in the barrel. The stub contains a female thread and includes a ratchet stop defined on the free end of the stub. A plunger includes a first end and a second end. A male thread is formed on one end of the plunger and is inserted into the barrel. A button is formed on the other end of the plunger outside the barrel. The male thread on the plunger screws into the female thread in said stub. One end of the male thread has a ratchet wing opposite to the ratchet stop. The ratchet wing and the ratchet stop are engaged with each other after the male thread is screwed into the stub. A connecting block includes an open end and a closed end. A female thread is defined in the open end to securely receive the external thread of the barrel. The closed end of the connecting block has a needle hub and a flange each extending therefrom. The flange is around the needle. The needle hub includes a top having a through hole defined therein to communicate with the open end of the connecting block.

3 Claims, 5 Drawing Sheets

BLOOD SYRINGE

BACKGROUND OF THE INVENTION

1. Field of the Invention

The present invention relates to a blood syringe, and more particularly to a blood syringe with a ratchet device to prevent the piston from detaching from the plunger while drawing blood.

2. Description of Related Art

As shown in FIG. 5, a conventional blood syringe in accordance with the prior art comprises a hollow barrel (50) with a connecting block (51), a plunger (60) with a piston (61) and a cap (70). The plunger (60) is received in the hollow barrel (50) and partially extends through the hollow barrel (50). The cap (70) closes the end of the connecting block (51) on the hollow barrel (50) opposite to the plunger (60).

An external thread (501) is formed on one end of the hollow barrel (50) and an internal circular flange (502) is formed inside the other end. The connecting block (51) has an open end and a closed end. The inside of the open end of the connecting block (51) is threaded and screws onto the external thread (501) on the hollow barrel (50). The closed end of the connecting block (51) includes a hollow needle hub (512) extending out from the center of the closed end and a flange (511) extending longitudinally out from the closed end around the needle hub (512). A through hole (513) is defined in the end of the needle hub (512). The through hole (513) communicates with the open end of the connecting block (51).

A male thread (602) is formed on one end of the plunger (60) and a button (603) is formed on the other end. A neck (601) is formed between the male thread (602) and the plunger (60). The plunger (60) is broken off at the neck (601) after drawing blood has been completed. The piston (61) has a hollow stub (611) extending from one end with an internal female thread (not numbered).

The cap (70) includes an open end to snugly fit over the flange (511) of the connecting block (51) and a closed end having a prong (71) extending inward. The prong (71) extends through the through hole (513) of the needle hub (512) when the cap (70) is attached to the connecting block (51).

However, carelessness by the technician while drawing blood may cause the piston (61) to detach from the plunger (60), and the blood in the hollow barrel (50) will flow back into the examinee's body. Also, since the cap (70) is simply pressed onto the connecting block (51), the cap (70) can easily be detached from the connecting block (51) if bumped.

The present invention has arisen to mitigate and/or obviate the disadvantage of the conventional blood syringe.

SUMMARY OF THE INVENTION

In accordance with one aspect of the present invention, a blood syringe with a ratchet device is provided. The plunger of the blood syringe has a male thread formed on one end. The base of the thread forms a ratchet wing having a vertical side and an inclined side along the male thread. A piston having a hollow stub extending from one end is slidably mounted in a hollow barrel. A female thread is defined in the stub to receive the male thread on the plunger. The top of the stub defines a ratchet stop having a vertical side and an inclined side each opposite to the vertical side and the inclined side of the ratchet wing. The ratchet wing and the ratchet stop are engaged with each other after the plunger screws into the stub so that the plunger can't reverse and detach from the piston.

Further benefits and advantages of the present invention will become apparent after a careful reading of the detailed description with appropriate reference to the accompanying drawings.

DETAILED DESCRIPTION OF THE INVENTION

Figure 1:
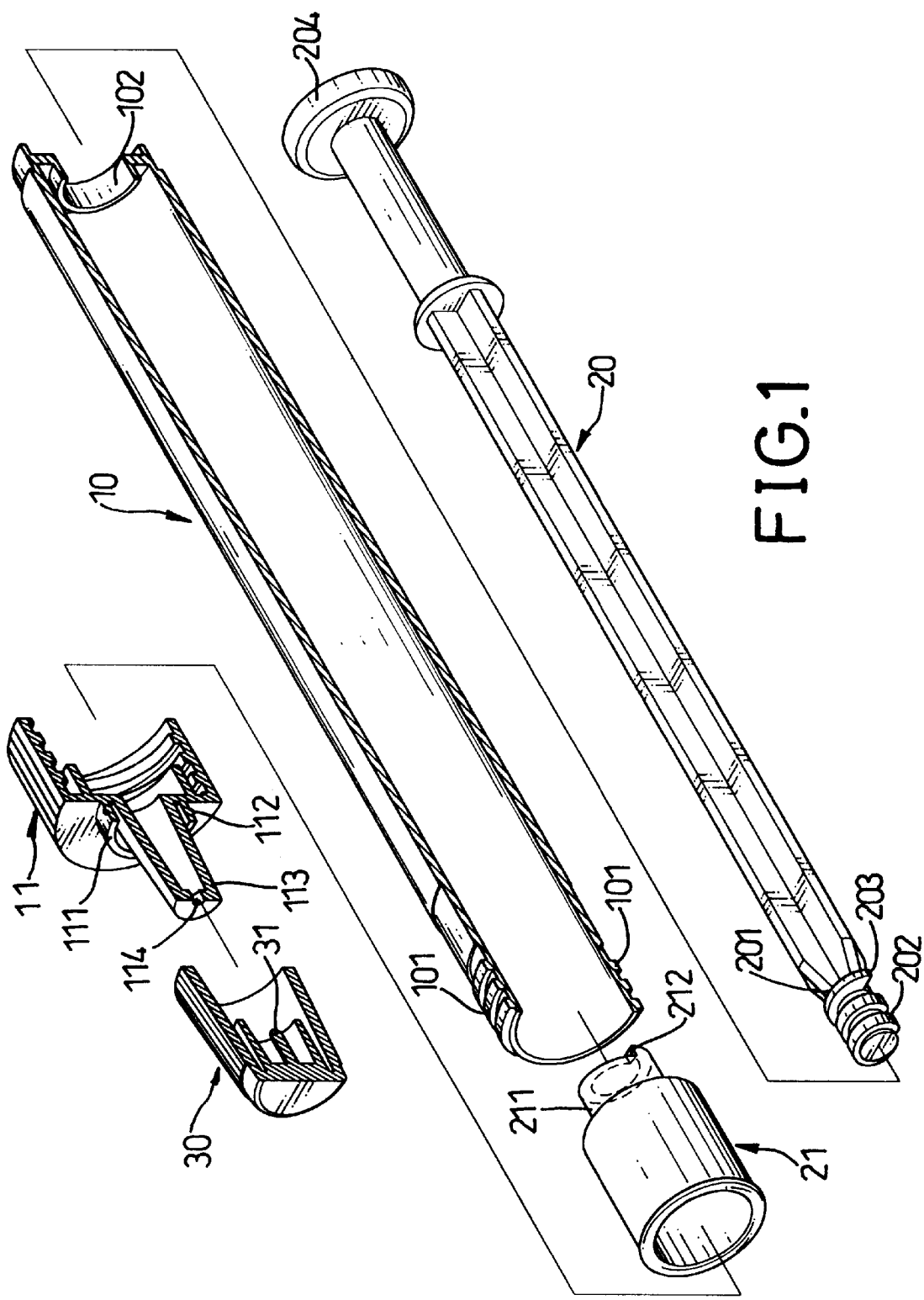
FIG. 1 is an exploded perspective view in partial section of a blood syringe in accordance with the present invention.
Figure 2:
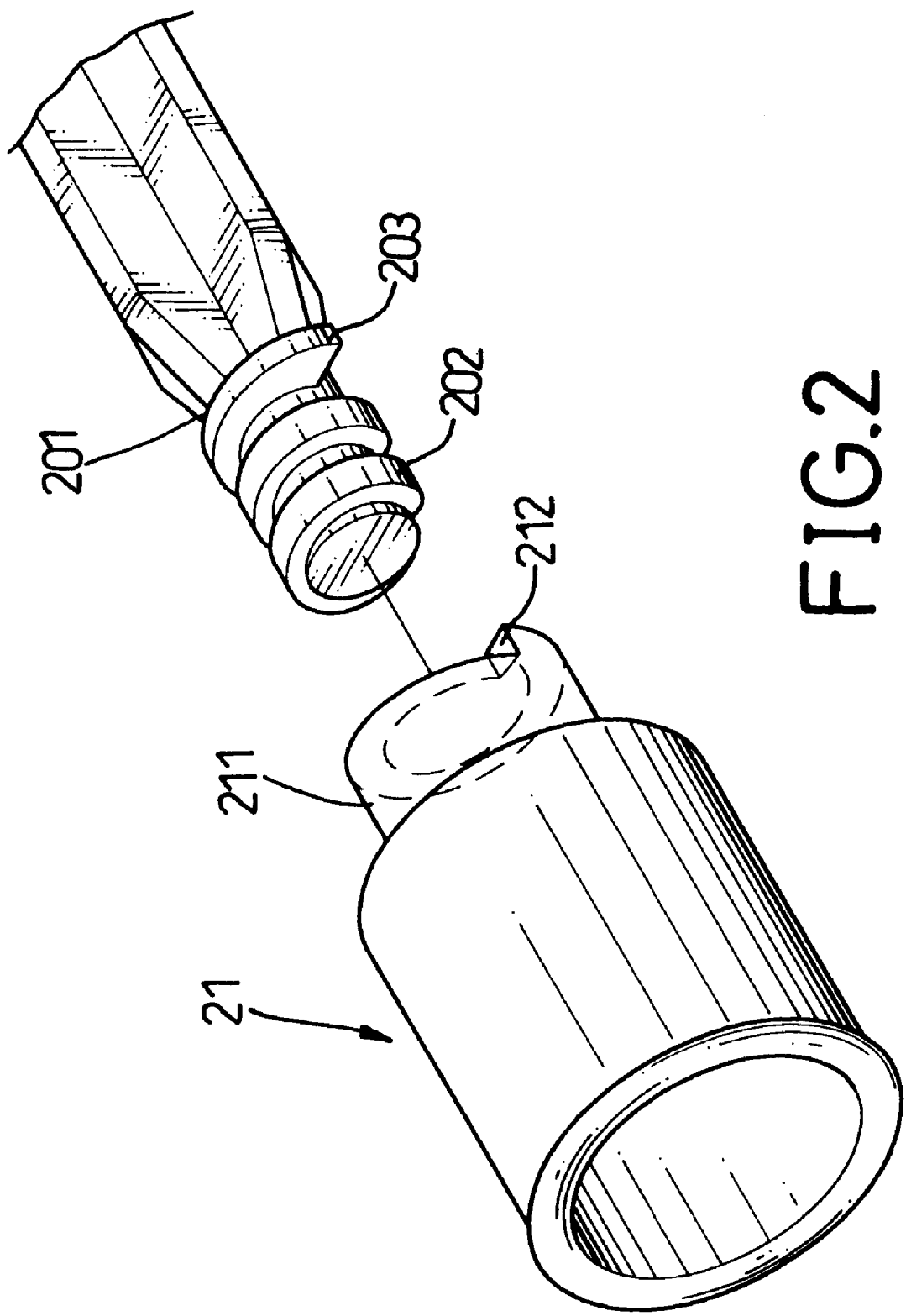
FIG. 2 is a partial exploded perspective view of the blood syringe in FIG. 1.

Referring to the drawings and initially to FIGS. 1–2, a blood syringe in accordance with the present invention comprises a hollow barrel (10) with a connecting block (11), a plunger (20) with a piston (21) and a cap (30). The plunger (20) is received in the hollow barrel (10) and partially extends through the hollow barrel (10). The cap (30) covers one end of the connecting block (11) opposite to the plunger (20).

An external thread (101) is formed on one end of the hollow barrel (10), and an internal flange (102) is formed on the inside of the other end of the hollow barrel (10) to prevent the piston (21) from coming out of that end of the barrel (10). The connecting block (11) has an open end and a closed end. The open end of the connecting block (11) has an internal thread and is screwed onto the external thread (101) of the hollow barrel (10). The closed end of the connecting block (11) includes a hollow needle hub (113) extending out from the center of the closed end and a flange (111) extending out longitudinally and around the needle hub (113). A through hole (114) is defined in the end of the needle hub (113). The through hole (114) communicates with the open end of the connecting block (11). Multiple bosses (1 12) extend out from the flange (111) of the connecting block (11).

A male thread (202) is formed on one end of the plunger (20) and a button (204) is formed on the other end. A ratchet wing (203) is defined at the top of the male thread (202) extends radially outward along the male thread (202) and has a vertical side and an inclined side. A neck (201) is formed between the male thread (202) and the plunger (20). The plunger (20) is broken off at the neck (201) after the syringe has been used. The piston (21) is slidably mounted in the hollow barrel (10) and has a hollow stub (211) extending from one end with an internal female thread. The diameter of the hollow stub (211) is smaller than that of the ratchet wing (203). A ratchet stop (212) has a vertical side and an inclined side each opposite to the vertical side, and the inclined side of the ratchet wing (203) is formed on the free end of the hollow stub (211). The ratchet wing (203) of the male thread (202) on the plunger (20) and the ratchet stop (212) on the stub (211) are engaged when the male thread (202) screws into the stub (211) after these two inclined sides of the ratchet wing (203) and the ratchet stop (212) slide over the top thereof.

Figure 3:
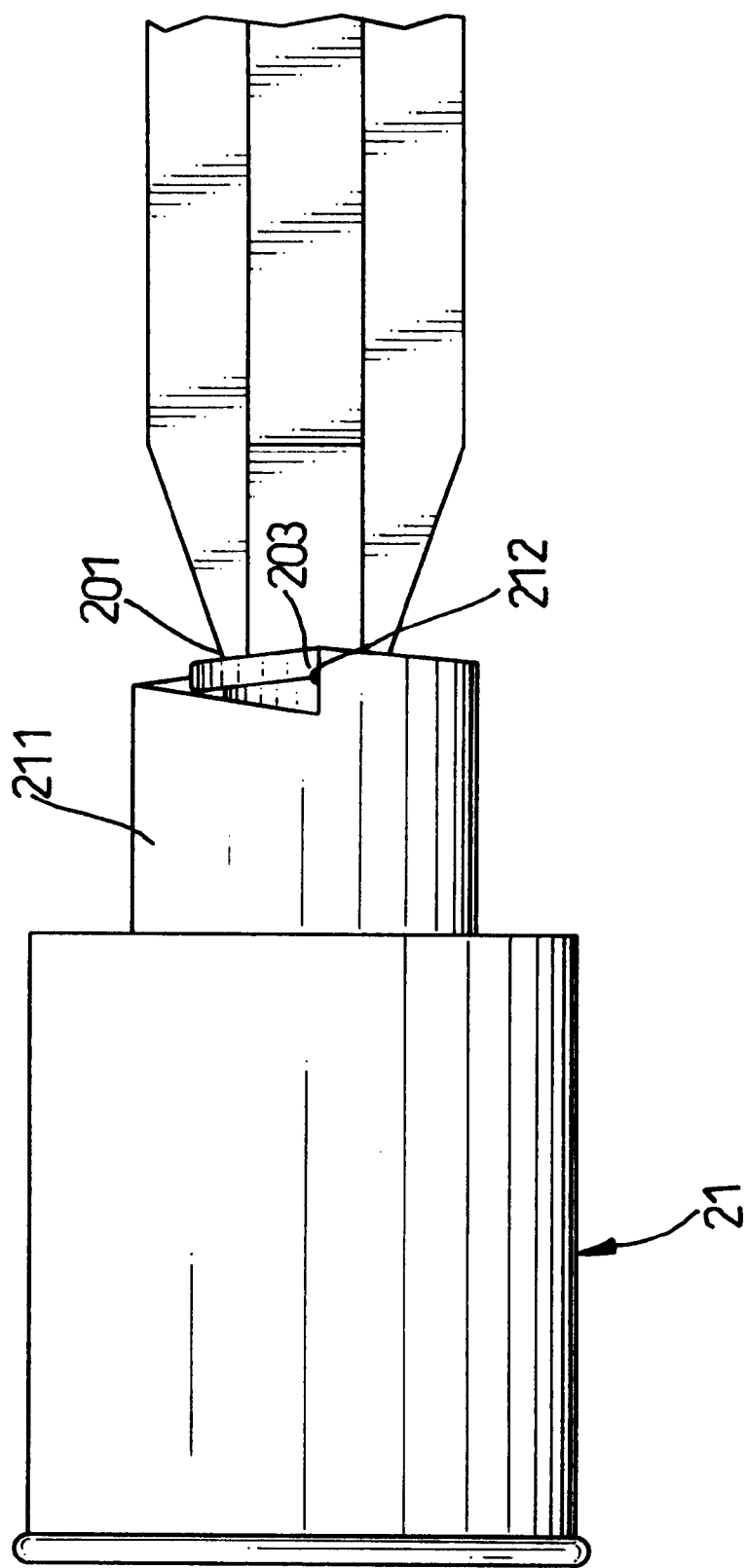
FIG. 3 is a partial side plan view of the blood syringe in FIG. 1.

The cap (30) includes an open end receiving the flange (111) of the connecting block (11) and a closed end with an internal prong (31). Referring to FIG. 3, the prong (31) extends through the through hole (114) of the needle hub (113) when the cap (30) is attached to the connecting block (11).

Figure 4:
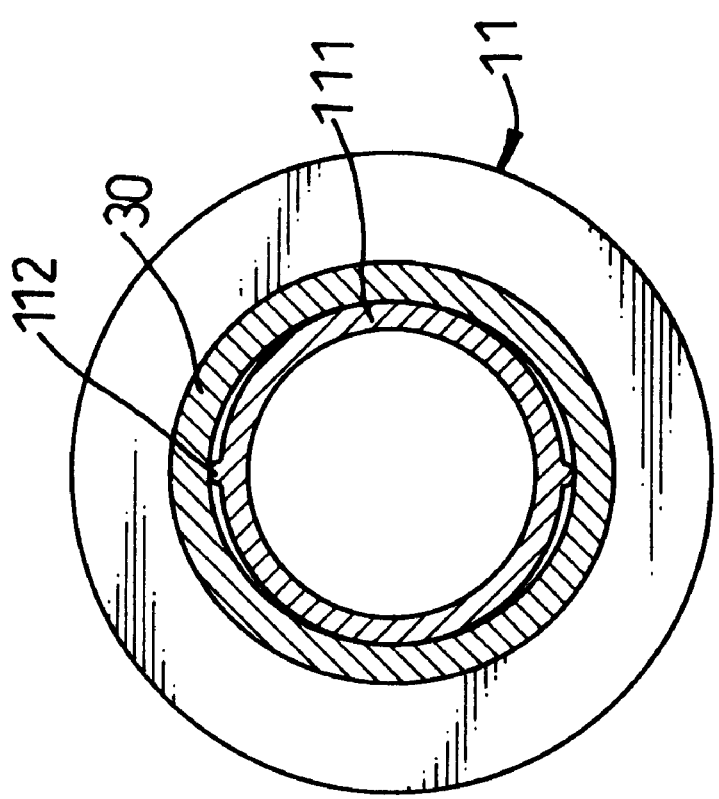
FIG. 4 is a front plan view in partial section of the cap and the connecting block in FIG. 1.
Figure 5:
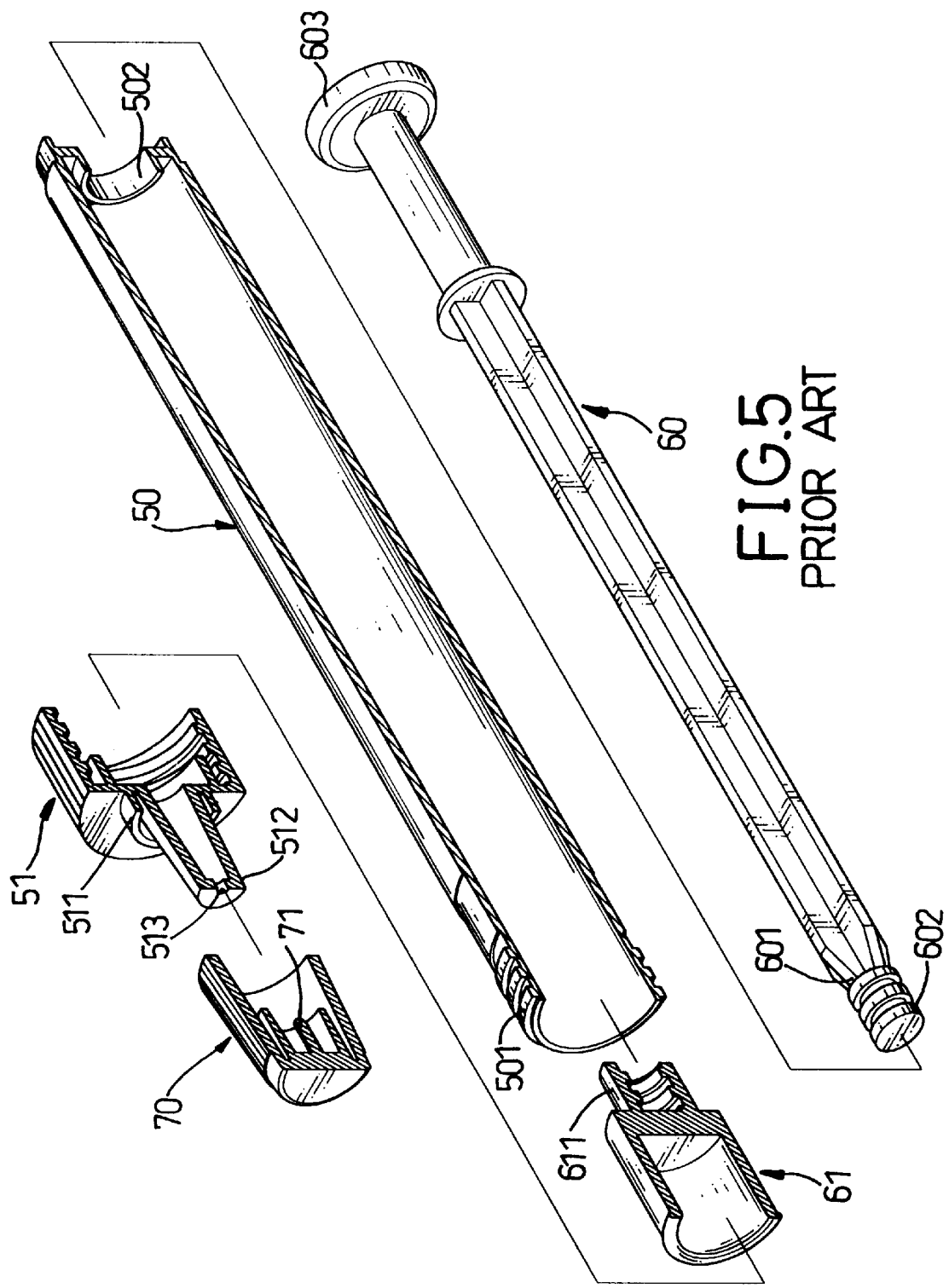
FIG. 5 is an exploded perspective view in partial section of a conventional blood syringe in accordance with the prior art.

Referring to FIGS. 3–4, the blood syringe in accordance with the present invention has several advantages.

1. The piston (21) can't detach from the plunger (20) because they are engaged each other and form a ratchet device thereby ensuring that the blood in the hollow barrel (10) does not reverse and flow back into the examinee while drawing blood.

2. The cap (30) is more securely attached to the connecting block (11) because the flange (111) of the connecting block (11) has multiple bosses (112) to abut the interior of the cap (30) and hold it more securely in place. Then the blood in the syringe is safer because the possibility of contamination is reduced.

Although the invention has been explained in relation to its preferred embodiment, it is to be understood that many other possible modifications and variations can be made without departing from the spirit and scope of the invention as hereinafter claimed.

What is claimed is:

1. A blood syringe comprising:

a hollow barrel (10) having a first end formed an external thread (101) formed on one end and a circular internal flange (102) formed inside the other end;

a piston (21) slidably mounted in said barrel (10) with a hollow stub (211) extending from one end of said piston (21), said stub (211) having an internal female thread formed therein and including a free end having a ratchet stop (212) defined thereon;

a plunger (20) with a male thread (202) formed one end inserted into said barrel (10), and a button (204) formed on the other end extending outside the barrel (10), said male thread (202) of said plunger (20) screwed into the female thread of said stub (211), one end of said male thread (202) having a ratchet wing (203) opposite to said ratchet stop (212), said ratchet wing (203) and said ratchet stop (212) engaged each other after said male thread (202) is screwed into said stub (211); and a connecting block (11) including a female thread defined in the open end to securely receive said external thread (101) of said barrel (10) and a closed end having a needle hub (113) and a flange (111) each extending longitudinally, said flange (111) being around said needle hub (113), and a through hole (114) defined through the end of the needle hub (113) to communicate with said open end of said connecting block.

2. The blood syringe in accordance with claim 1 further comprising a cap (30), said cap (30) including an open end to receive said flange (111) of said connecting block (11) and a closed end having an internal prong (31) received in said through hole (114).

3. The blood syringe in accordance with claim 1, wherein said flange (111) of said connecting block (11) includes multiple bosses (112) formed thereon to abut the interior of said open end of said cap (30).

* * * * *